United States Patent
Liu

(10) Patent No.: US 9,441,258 B2
(45) Date of Patent: Sep. 13, 2016

(54) ENZYME IMMOBILIZATION BY CROSSLINKING

(71) Applicant: Verily Life Sciences LLC, Mountain View, CA (US)

(72) Inventor: Zenghe Liu, Mountain View, CA (US)

(73) Assignee: Verily Life Sciences LLP, Mountain View, CA (US)

( * ) Notice: Subject to any disclaimer, the term of this patent is extended or adjusted under 35 U.S.C. 154(b) by 586 days.

(21) Appl. No.: 13/930,890

(22) Filed: Jun. 28, 2013

(65) Prior Publication Data

US 2015/0001074 A1 Jan. 1, 2015

(51) Int. Cl.
*G01N 27/40* (2006.01)
*C12Q 1/00* (2006.01)

(52) U.S. Cl.
CPC ............. *C12Q 1/002* (2013.01); *C12Q 1/003* (2013.01); *C12Q 1/006* (2013.01); *G01N 27/40* (2013.01)

(58) Field of Classification Search
None
See application file for complete search history.

(56) References Cited

U.S. PATENT DOCUMENTS

| | | | |
|---|---|---|---|
| 4,929,313 A | 5/1990 | Wrighton | |
| 5,543,326 A | 8/1996 | Heller et al. | |
| 6,653,358 B2 | 11/2003 | Bruza | |
| 6,654,625 B1 * | 11/2003 | Say | A61B 5/1486 600/345 |
| 7,959,791 B2 | 6/2011 | Kajer | |
| 8,385,998 B2 | 2/2013 | Zhang | |
| 8,437,829 B2 | 5/2013 | Mao | |
| 2004/0256227 A1 | 12/2004 | Shin | |
| 2007/0114138 A1 | 5/2007 | Krasteva et al. | |
| 2008/0281178 A1 | 11/2008 | Chuang | |
| 2009/0280181 A1 * | 11/2009 | Slager | A61K 9/0024 424/484 |
| 2011/0136929 A1 | 6/2011 | Chow | |
| 2012/0201755 A1 | 8/2012 | Rozakis | |
| 2012/0245444 A1 | 9/2012 | Otis | |
| 2012/0296186 A1 * | 11/2012 | Ouyang | A61B 5/14865 600/347 |
| 2013/0011460 A1 | 1/2013 | Liu | |

FOREIGN PATENT DOCUMENTS

| | | | | |
|---|---|---|---|---|
| EP | 1927602 A1 | 6/2008 | | |
| MY | WO2012115501 A1 | 8/2012 | | |
| WO | WO 2012/161735 A1 * | 11/2012 | | A61B 5/05 |
| WO | WO2012161735 A1 | 11/2012 | | |

OTHER PUBLICATIONS

Product information sheet for Polymer Source product No. P8382-4VPEO acccessed Jan. 13, 2015.*

(Continued)

*Primary Examiner* — Luan Van
*Assistant Examiner* — Steven Rosenwald
(74) *Attorney, Agent, or Firm* — McDonnell Boehnen Hulbert & Berghoff

(57) ABSTRACT

An analyte sensor for the continuous or semi-continuous monitoring of physiological parameters and a method for making the analyte sensor are disclosed. In one aspect, the analyte sensor includes an electrode, a sensing layer in contact with a surface of the electrode, and a protective membrane. The sensing layer is a crosslinked, hydrophilic copolymer including poly(alkylene oxide) and poly(vinyl pyridine), and an analyte sensing component is immobilized within the crosslinked, hydrophilic copolymer. The protective membrane is a crosslinked, hydrophilic copolymer including alkylene oxide, vinyl pyridine and styrene units. The method involves the formation of a sensing layer on a surface of an electrode, followed by the formation of a protective membrane on a surface of the sensing layer.

19 Claims, 1 Drawing Sheet

(56) References Cited

OTHER PUBLICATIONS

Product information sheet for Polymer Source product No. P14260-EOS4VPran accessed Jan. 13, 2015.*
International Search Report issued in connection with co-pending International Patent Application No. PCT/US2014/044613, ISA/KR dated Oct. 23, 2014, 6 pgs.
Written Opinion issued in connection with co-pending International Patent Application No. PCT/US2014/044613, ISA/KR dated Oct. 23, 2014, 5 pgs.

* cited by examiner

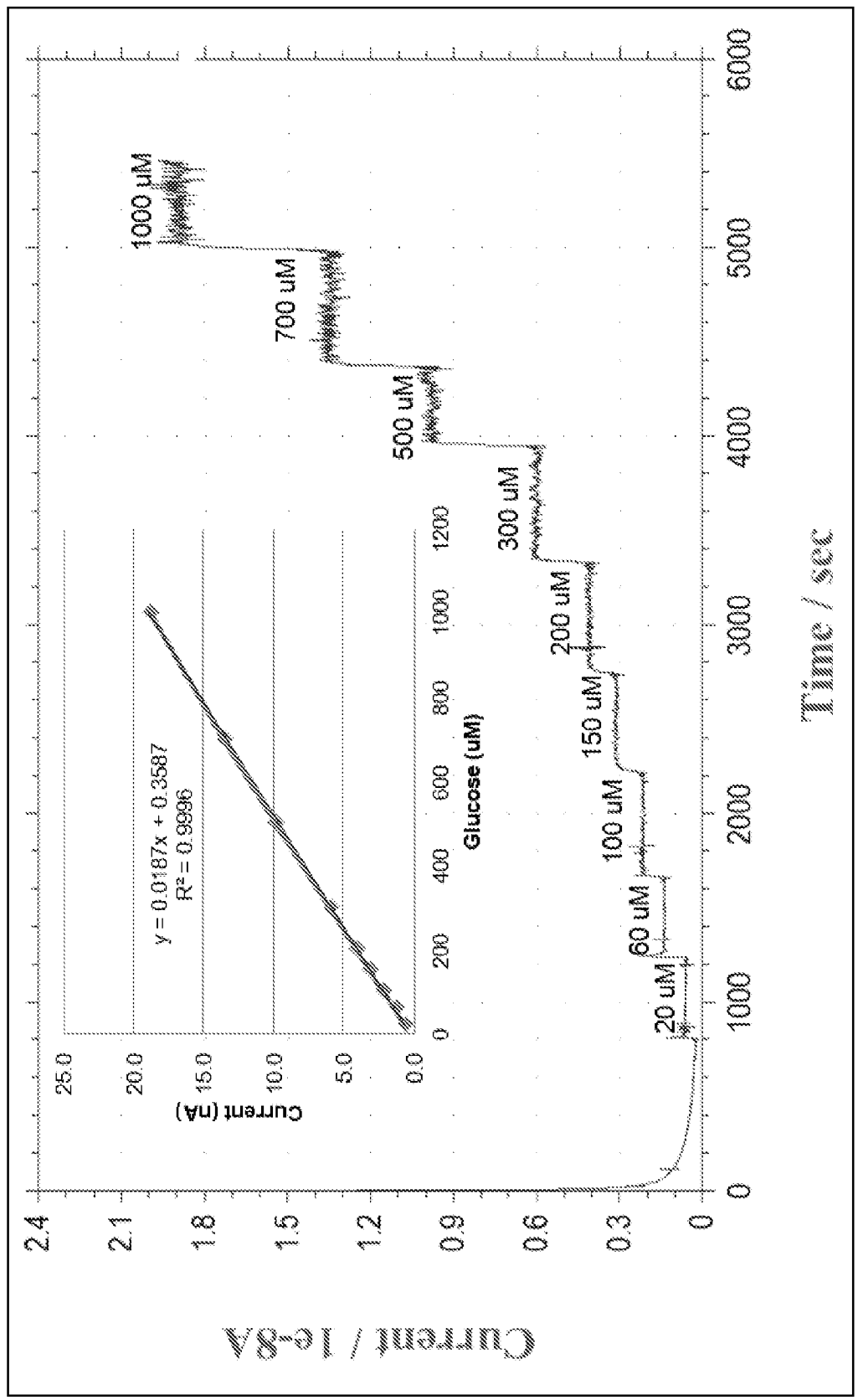

ENZYME IMMOBILIZATION BY CROSSLINKING

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, an analyte sensor is disclosed. The analyte sensor includes a sensing layer in contact with a surface of an electrode, and a protective membrane. The sensing layer is a crosslinked, hydrophilic copolymer including poly(alkylene oxide) and poly(vinyl pyridine) and an analyte sensing component immobilized within the crosslinked, hydrophilic copolymer. The protective membrane is a crosslinked, hydrophilic copolymer including alkylene oxide, vinyl pyridine and styrene units.

In another aspect, a method for forming an analyte sensor is disclosed. The method involves forming a first solution of a hydrophilic copolymer, a crosslinking agent and an analyte sensing component, and depositing the first solution onto a surface of an electrode. The hydrophilic copolymer of the first solution includes poly(alkylene oxide) and poly(vinyl pyridine), and is subjected to conditions suitable to promote chemical reaction between the crosslinking agent and the hydrophilic copolymer, providing a sensing layer. A second solution of a hydrophilic copolymer and a crosslinking agent is formed and deposited onto the surface of the sensing layer. The hydrophilic copolymer of the second solution includes alkylene oxide, vinyl pyridine and styrene units, and is subjected to conditions suitable to promote chemical reaction between the crosslinking agent and the hydrophilic copolymer, providing a protective membrane.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 is a graph of current produced by an example glucose sensor at glucose concentrations of 20 μm to 1,000 μm in phosphate buffered saline (PBS). A linear relationship between current and glucose concentration was observed (see inset graph).

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In one aspect, an analyte sensor is disclosed. The analyte sensor can include: a sensing layer in contact with a surface of an electrode, where the sensing layer could be a crosslinked, hydrophilic copolymer with alkylene oxide (AO) and vinyl pyridine (VP) units, and an analyte sensing component immobilized within the copolymer; and a protective membrane, where the protective membrane could be a crosslinked, hydrophilic copolymer with alkylene oxide, vinyl pyridine (VP) and styrene (S) units.

In some embodiments, the analyte sensor is an enzyme-based biosensor. These devices are able to convert an analyte-concentration-dependent biochemical reaction signal into a measurable physical signal, such as an optical or electrical signal. The biosensors can be used in the detection of analytes in clinical, environmental, agricultural and biotechnological applications. Analytes that can be measured in clinical assays of fluids of the human body include, for example, glucose, lactate, cholesterol, bilirubin and proteins, lipids and electrolytes. The detection of analytes in biological fluids, such as blood, tear film, or intestinal fluid, can be important in the diagnosis and the monitoring of many diseases.

In some embodiments, the analyte sensor is a component of a body-mountable device, such as an eye-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may include a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may include a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from a conductive material and can be patterned by a process used for patterning such materials, such as deposition or photolithography, for example. The conductive materials can be, for example, gold, platinum, palladium, titanium, carbon, copper, silver/ silver-chloride, conductors formed from noble materials, metals, or any combinations of these materials. Other materials can also be envisioned.

The sensing layer of the analyte sensor can be a crosslinked, hydrophilic copolymer with a backbone of poly(alkylene oxide) and poly(vinyl pyridine) and an analyte sensing component, such as an enzyme, immobilized within the copolymer. As discussed in greater detail below, the crosslinks are covalent linkages between same or different copolymer backbones and the immobilized enzyme can be embedded in or covalently linked to the copolymer backbones. Various conformations and compositions of these units can provide the desired properties of the sensing layer, which include hydrophilicity and the ability to immobilize an analyte sensing component.

In some embodiments, the crosslinked, hydrophilic copolymer of the sensing layer can be a block copolymer. The block copolymer can be various types of block copolymer, such as diblock, triblock, tetrablock, or multiblock copolymer. In some examples, the block copolymer has one or more intermediate non-repeating subunits, or junction blocks. In other embodiments, the copolymer can be an alternating, periodic, statistical or graft copolymer. In some instances, the copolymer includes two distinct monomer units, such as a diblock copolymer. In other instances, the copolymer has three distinct monomer units, such as a terpolymer.

The poly(alkylene oxide) of the backbone of the crosslinked, hydrophilic copolymer of the sensing layer can be any suitable poly(alkylene oxide), such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinked, hydrophilic copolymer is a block copolymer including blocks of two or three different poly(alkylene oxide) polymers. In certain embodiments, the poly(alkylene oxide) is block copolymer of poly(ethylene glycol) and poly(propylene glycol). In other embodiments, the poly(alkylene oxide) is poly(ethylene glycol).

In some embodiments, the crosslinked, hydrophilic copolymer of the sensing layer includes a copolymer of poly(ethylene glycol) (PEG) and poly(vinyl pyridine) (PVP). The copolymer of PEG and PVP can be a block copolymer, having one or more blocks each of PEG and PVP. In some embodiments, the sensing layer includes a diblock copolymer of PEG and PVP.

The ratio of alkylene oxide to vinyl pyridine in the crosslinked, hydrophilic copolymer of the sensing layer can be varied depending on the desired properties of the crosslinked, hydrophilic copolymer of the sensing layer. In some instances, the PEG block can be longer than the PVP block, thus modulating the hydrophilic/hydrophobic character of the material, and providing an environment for keeping the analyte sensing component, such as an enzyme (e.g., glucose oxidase), immobilized and/or stable, and accessible by the analyte of interest.

In some embodiments, the crosslinked, hydrophilic, diblock copolymer of the sensing layer has the formula:

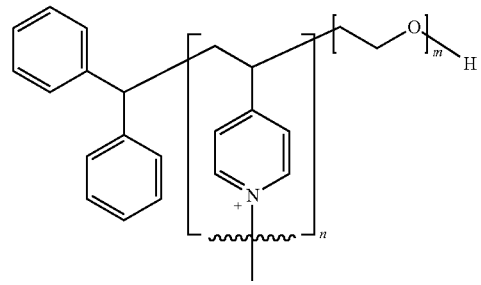

wherein n and m are independently selected to provide poly(vinyl pyridine) and poly(ethylene glycol) blocks each having number average molecular weights ($M_n$) of about 500 to about 10,000. In other embodiments, n is an average value of from about 5 to about 100, and m is an average value of from about 5 to about 250. For ease of illustration, the pyridine nitrogen of the poly(vinyl pyridine) of the sensing layer is drawn as being covalently bound to a crosslink (i.e., crosslinked). One of skill in the art will recognize that, in practice, not every pyridine nitrogen of the sensing layer may be crosslinked. The cross-links are not included in the molecular weight determination.

The properties of the crosslinked, hydrophilic, diblock copolymer of the sensing layer can be adjusted to achieve desirable properties, such as hydrophilicity, permeability, number of crosslinkable groups, and the ability to immobilize the analyte sensing component. In certain embodiments, n is selected so that the $M_n$ of the poly(vinyl pyridine) blocks falls within a range in Table 1, and m is selected so that the $M_n$ of the poly(ethylene glycol) blocks falls within a range in the Table 2. For example, the crosslinked, hydrophilic, diblock copolymer of the sensing layer can have a poly(vinyl pyridine) block with an $M_n$ between about 5,000 and about 6,000, and a poly(ethylene glycol) block with an $M_n$ between about 8,000 and about 9,000.

TABLE 1

$M_n$ range of poly(vinyl pyridine) block (values are approximate).

| Low | High |
| --- | --- |
| 500 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

TABLE 2

$M_n$ range of poly(ethylene glycol) block (values are approximate).

| Low | High |
| --- | --- |
| 500 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |

TABLE 2-continued

M$_n$ range of poly(ethylene glycol) block (values are approximate).

| Low | High |
| --- | --- |
| 8,000 | 9,000 |
| 9,000 | 10,000 |

The properties of the crosslinked, hydrophilic, diblock copolymer of the sensing layer can be adjusted by varying the values of n and m. In some embodiments, the ratio of the average number of vinyl pyridine units (corresponding to n) to the average number of ethylene glycol units (corresponding to m) can be selected from Table 3. For example, when the average number of vinyl pyridine units is approximately 2,000, and the average number of ethylene glycol units can be approximately 4,000, the resulting ratio of vinyl pyridine units to ethylene glycol units is approximately 1:2.

TABLE 3

Ratio of vinyl pyridine units to ethylene glycol units (all values are approximate).

| vinyl pyridine | ethylene glycol |
| --- | --- |
| 1 | 1 |
| 1 | 2 |
| 1 | 3 |
| 1 | 4 |
| 1 | 5 |
| 2 | 3 |
| 3 | 4 |
| 1 | 10 |
| 1 | 20 |
| 1 | 50 |
| 1 | 100 |

The analyte sensing component of the sensing layer is a moiety that can be immobilized in the crosslinked, hydrophilic copolymer and interact with a corresponding analyte of interest. In some embodiments, the analyte sensing component is an enzyme.

In some embodiments, the immobilized analyte sensing component can be embedded in the polymer matrix of the crosslinked, hydrophilic copolymer of the sensing layer. The embedded sensing component does not have a covalent linkage to the copolymer, but is surrounded by the crosslinks and copolymer backbone of the crosslinked, hydrophilic copolymer.

In other embodiments, the immobilized analyte sensing component can be covalently bound to the crosslinked, hydrophilic copolymer of the sensing layer. The covalent bond can be through a linker, which can have the same formula as the crosslinks of the crosslinked, hydrophilic copolymer. Thus, in some instances, the analyte sensing component has one or more groups that can chemically react with the crosslink precursor, such as when the analyte sensing component is an enzyme having one or more amino, carboxyl, hydroxyl or thiol groups available for reaction with the crosslink precursor. As a result, in some embodiments, the analyte sensing component has one or more oxygen, nitrogen or sulfur atoms covalently bound, optionally through a linker, to the copolymer backbone of the sensing layer.

In certain embodiments, the sensing layer includes a mixture of immobilized analyte sensing components, where some are embedded in the polymer matrix of the crosslinked, hydrophilic copolymer, and some are covalently bound, optionally through a linker, to the copolymer backbone.

The analyte sensing component of the sensing layer can be selected to monitor physiological levels of a specific analyte. For example, glucose, lactate, cholesterol and various proteins and lipids can be found in body fluids including, for example, tear film, and can be indicative of medical conditions that can benefit from continuous or semi-continuous monitoring.

The enzyme immobilized in the sensing layer of the analyte sensor can be selected based on the analyte desired to be monitored. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a sensing layer including glucose oxidase ("GOx") can be situated around the working electrode to catalyze a reaction with glucose (e.g., β-D-glucose) to produce hydrogen peroxide ($H_2O_2$). As shown below, the hydrogen peroxide can then be oxidized at the working electrode to releases electrons to the working electrode, which generates a current.

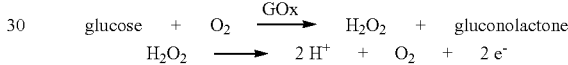

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In other embodiments, the analyte sensing component can be glucose dehydrogenase (GDH). In certain instances, the use of GDH can require the addition of a cofactor such as flavin adenine dinucleotide (FAD), nicotinamide adenine dinucleotide (NAD), flavin mononucleotide, pyrroloquinoline quinone (PQQ) or a coenzyme.

The protective membrane can be a crosslinked, hydrophilic copolymer including a backbone of alkylene oxide units, vinyl pyridine units and/or units of other polymerizable moieties such as styrene, methacrylate, and acrylate. The protective membrane controls the equilibrium between the concentration of the analyte (e.g., glucose) in the sample solution, and the analyte concentration in the proximity of the sensing layer electrode surface. When all of the analyte arriving at the sensing layer is consumed, the measured output signal can be linearly proportional to the flow of the analyte and thus to the concentration of the analyte. However, when the analyte consumption is limited to the kinetics of chemical or electrochemical activities in the sensing layer, the measured output signal may no longer be controlled by the flow of analyte and may no longer be linearly proportional to the flow or concentration of the analyte. In this case, only a fraction of the analyte arriving at the sensing layer is consumed before the sensor becomes saturated, whereupon the measured signal stops increasing, or increases only slightly, with an increasing concentration of the analyte. The protective membrane can reduce the flow of the analyte to the sensing layer so the sensor does not become saturated and can therefore effectively enable a wider range of analyte concentrations to be measured.

The alkylene oxide, vinyl pyridine and/or other polymerizable units of the protective membrane can be varied to produce desired properties of the protective membrane. For example, flow of the analyte across the membrane can be dependent on the specific analyte being monitored, and thus, the protective membrane can be altered to obtain optimal properties for monitoring a specific analyte. In some applications, the hydrophilicity of the protective membrane can be increased by increasing the ratio of alkylene oxide units to vinyl pyridine and/or other units (e.g., styrene). Alternatively, a less hydrophilic membrane can be obtained by increasing the ratio of vinyl pyridine and/or other units (e.g., styrene) to alkylene oxide units.

In some embodiments, the crosslinked, hydrophilic copolymer of the protective membrane includes a copolymer of alkylene oxide, vinyl pyridine and styrene. The copolymer of alkylene oxide, vinyl pyridine and styrene can be a block copolymer, having one or more blocks each of poly(alkylene oxide) (PAO), poly(vinyl pyridine) (PVP) and poly( ) (PS). In some embodiments, the crosslinked, hydrophilic copolymer of the protective membrane includes a triblock copolymer of PAO, PVP and PS. In other embodiments, the crosslinked, hydrophilic copolymer of the protective membrane includes a diblock copolymer, where one block includes PAO and the other block includes a random copolymer of vinyl pyridine and styrene. In other embodiments, the crosslinked, hydrophilic copolymer can be a PAO capped random copolymer of vinyl pyridine and styrene. In some examples, the PAO caps both ends of the random copolymer, while in other instances one end of the random copolymer is capped with PAO.

The poly(alkylene oxide) of the backbone of the crosslinked, hydrophilic copolymer of the protective membrane can be poly(ethylene glycol), poly(propylene glycol), poly (butylene oxide) or mixture thereof, such as a copolymer including a combination of two or three alkylene oxide units. In some embodiments, the poly(alkylene oxide) of the crosslinked, hydrophilic copolymer can be a block copolymer including blocks of two or three poly(alkylene oxide) polymers. In certain embodiments, the poly(alkylene oxide) can be block copolymer of poly(ethylene glycol) and poly (propylene glycol).

In some embodiments, the crosslinked, hydrophilic copolymer of the protective membrane can be a diblock copolymer, where one block includes PEG and the other block includes PVP and PS. In certain embodiments, the diblock copolymer can have one block that includes PEG and the other block that includes a random copolymer of vinyl pyridine and styrene. In other embodiments, the diblock copolymer can be a PEG capped random copolymer of vinyl pyridine and styrene. In some examples, the PEG caps both ends of the random copolymer, while in other instances one end of the random copolymer is capped with PEG.

The ratio of alkylene oxide units to vinyl pyridine units to units of other polymerizable moieties, such as, styrene, methacrylate and acrylate in the crosslinked, hydrophilic copolymer of the protective membrane can be varied depending on the desired properties of the protective membrane. In some embodiments, the crosslinked, hydrophilic copolymer can have a lesser proportion of alkylene oxide to vinyl pyridine and/or other polymerizable moieties, such as, styrene, methacrylate and acrylate, to provide a protective layer that is less hydrophilic and offers increased mechanical strength to maintain the integrity of the sensing chemistry during its use in aqueous environment.

In some embodiments, the crosslinked, hydrophilic copolymer of the protective membrane has similar a structure and/or properties as the crosslinked, hydrophilic copolymer of the sensing layer. Similar properties between the copolymers of the sensing layer and protective membrane can enhance compatibility between the sensing layer and the protective membrane.

In some embodiments, the crosslinked, hydrophilic, diblock copolymer of the protective membrane has the formula:

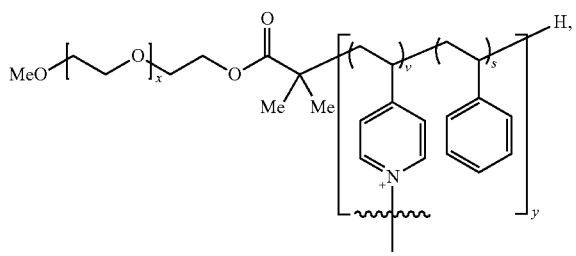

wherein x, y, v and s are selected such that the poly(ethylene glycol) block and the vinyl pyridine/styrene copolymer block each have a number average molecular weight ($M_n$) of about 1,000 to about 100,000. In other embodiments, x is an average value of from about 25 to about 250, and y is an average value of from about 5 to about 50. For ease of illustration, the pyridine nitrogen of the poly(vinyl pyridine) of the protective membrane is drawn as being covalently bound to a crosslink (i.e., crosslinked), which is described below. One of skill in the art will recognize that, in practice, not every pyridine nitrogen of the protective membrane will be crosslinked.

The properties of the crosslinked, hydrophilic, diblock copolymer of the protective membrane can be adjusted to achieve desirable properties, such as the hydrophilicity, permeability, number of crosslinkable groups, or thickness of the protective membrane. In certain embodiments, x, can be selected such that the $M_n$ of the poly(ethylene glycol) block falls within a range in Table 4, and y can be selected such that the $M_n$ of the vinyl pyridine/styrene copolymer block falls within a range in Table 5. For example, the crosslinked, hydrophilic, diblock copolymer of the protective membrane can have a poly(ethylene glycol) block with an $M_n$ between about 5,000 and about 10,000, and a vinyl pyridine/styrene copolymer block with an $M_n$ between about 40,000 and about 50,000.

TABLE 4

| $M_n$ range of poly(ethylene glycol) block (values are approximate). | |
|---|---|
| Low | High |
| 500 | 1,000 |
| 1,000 | 2,000 |
| 2,000 | 3,000 |
| 3,000 | 4,000 |

TABLE 4-continued

M$_n$ range of poly(ethylene glycol) block (values are approximate).

| Low | High |
|---|---|
| 4,000 | 5,000 |
| 5,000 | 6,000 |
| 7,000 | 8,000 |
| 8,000 | 9,000 |
| 9,000 | 10,000 |

TABLE 5

M$_n$ range of vinyl pyridine/styrene copolymer block (values are approximate).

| Low | High |
|---|---|
| 5,000 | 10,000 |
| 10,000 | 20,000 |
| 20,000 | 30,000 |
| 30,000 | 40,000 |
| 40,000 | 50,000 |
| 50,000 | 60,000 |
| 70,000 | 80,000 |
| 80,000 | 90,000 |
| 90,000 | 100,000 |

The properties of the crosslinked, hydrophilic, diblock copolymer of the protective membrane can also be adjusted by varying of the values of x, y, v and s. In some embodiments, the ratio of the average number of ethylene glycol units to the average number of vinyl pyridine units to the average number of styrene units can be selected from Table 6. For example, when the average number of ethylene glycol units is approximately 2,000, the average number of vinyl pyridine units is approximately 5,000, and the average number of styrene units is approximately 1,000, the ratio of ethylene glycol units to vinyl pyridine units to styrene units is approximately 2:5:1.

TABLE 6

Ratio of ethylene glycol units to vinyl pyridine units to styrene units (all values are approximate).

| ethylene glycol | vinyl pyridine | styrene |
|---|---|---|
| 1 | 1 | 1 |
| 1 | 3 | 2 |
| 2 | 3 | 1 |
| 3 | 5 | 2 |
| 2 | 5 | 1 |
| 3 | 10 | 2 |
| 1 | 10 | 1 |
| 5 | 20 | 5 |
| 5 | 5 | 1 |
| 10 | 10 | 5 |
| 10 | 20 | 1 |
| 20 | 50 | 3 |
| 1 | 5 | 1 |
| 3 | 10 | 2 |

The thickness of the protective membrane can vary depending on the desired properties of the analyte sensor. The thickness of the protective membrane, as measured from the top of the sensing layer to the top of the protective membrane, can play an important role in regulating the flow of the analyte to the sensing layer. Depending on the copolymers used in the sensing layer and the protective membrane, and the type of analyte sensing component used, the thickness of the protective membrane can be from less than about 1 µm to about 20 µm. In some instances, the membrane can be less than 1 µm in thickness, where in other applications the membrane can be about 1 µm to about 10 µm in thickness. In certain applications, the membrane can be about 1 µm to about 3 µm in thickness, where in other applications the membrane can be about 3 µm to about 7 µm or about 7 µm to about 10 µm in thickness. In some embodiments, the protective membrane can be about 2 µm in thickness.

The crosslinks of the copolymer of the sensing layer and protective membrane are fragments that can result from the reaction of molecules (i.e., crosslinking agents) having two or more reactive groups, such as bi-, tri-, or tetra-functional groups, that react with one or more reactive groups of the copolymer. The reactive groups of the copolymer include carboxyl, hydroxyl, thiol, pyridyl and amino groups. The crosslinks of the sensing layer and protective membrane can be of the same structure, but in some instances, have different structures. The crosslinks of the sensing layer and protective membrane share similar characteristics, however, and for simplicity, will herein be referred to as "the crosslinks".

In some embodiments, the immobilized analyte sensing component can be covalently bound through a linker to the backbone of the crosslinked, hydrophilic copolymer of the sensing layer. The linker can be a fragment resulting from the reaction the crosslinking agent with one or more reactive groups of the analyte sensing component. The reactive groups of the copolymer include carboxyl, hydroxyl, thiol and amino groups. Thus, the linker covalently bonding the analyte sensing component to the copolymer backbone of the sensing layer can have the same structure as the crosslinks as described herein.

In some embodiments, the crosslinks are derived from crosslinking agents containing two or more epoxide groups. Chemical reaction of the epoxides with the crosslinkable functionalities of the copolymer of the sensing layer and/or the copolymer of the protective membrane can proceed through nucleophilic attack of the crosslinkable functionality at the electrophilic epoxide carbon atom, providing a crosslink containing two or more secondary alcohol moieties. For example, a copolymer having nitrogen functionalities, such as a pyridine group, can react with a crosslinking agent having epoxide groups to provide crosslinks containing β-hydroxy amine functionalities.

In some embodiments, the crosslinks include poly(ethylene glycol) (PEG). For example, the crosslinks can be of the formula:

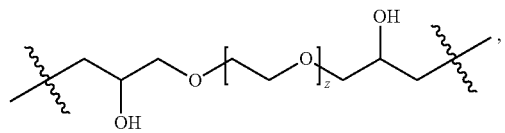

wherein z is 0, 1, 2, 3, 4, 5, 6, 7, 8, 9 or 10.

In certain embodiments, z is an average value of from about 5 to about 250.

In other embodiments, z is such that the number average molecular weight (M$_n$) of the PEG portion of the crosslinks is about 200 to about 10,000. For example, z can be selected such that the M$_n$ of the PEG portion of the crosslinks falls within a range in Table 7:

TABLE 7

M$_n$ range of the poly(styrene) (PEG) of the crosslinks (values are approximate).

| Low | High |
|---|---|
| 100 | 500 |
| 500 | 1,000 |
| 1,000 | 2,000 |
| 2,000 | 3,000 |
| 3,000 | 4,000 |
| 4,000 | 5,000 |
| 5,000 | 6,000 |
| 6,000 | 7,000 |
| 7,000 | 8,000 |
| 8,000 | 9,000 |
| 9,000 | 10,000 |

Suitable crosslinks are derived from, for example, diglycidyl ether, N,N-diglycidyl-4-glycidyloxyaniline, and diethylene glycol diglycidyl ether.

In another aspect, a method for making an analyte sensor is disclosed. The method can involve:
a) forming a first solution including a first hydrophilic copolymer, a first crosslinking agent and an analyte sensing component, where the first hydrophilic copolymer includes poly(alkylene oxide) and poly(vinyl pyridine);
b) depositing the first solution onto a surface of an electrode;
c) subjecting the first solution to conditions suitable to promote chemical reaction between the first crosslinking agent and the first hydrophilic copolymer (i.e., curing) to provide a sensing layer;
d) forming a second solution of a second hydrophilic copolymer and a second crosslinking agent, where the second hydrophilic copolymer includes units of alkylene oxide, vinyl pyridine and styrene;
e) depositing the second solution onto a surface of the sensing layer; and
f) subjecting the second solution to conditions suitable to promote chemical reaction between the second crosslinking agent and the second hydrophilic copolymer (i.e., curing) to provide a protective membrane.

In some embodiments, the first solution can be formed on a surface of an electrode. For example, each component, or a combination of one or more components, can be individually deposited. Similarly, the second solution can formed on a surface of the sensing layer.

In certain embodiments, the first solution includes a first hydrophilic copolymer, a first crosslinking agent and an analyte sensing component. The ratio of these three components can vary depending on the desired properties of the resulting sensing layer. In some examples, the solution can be about 10% by weight to about 40% by weight first hydrophilic copolymer, about 20% by weight to about 30% by weight first crosslinking agent, and about 20% by weight to about 70% by weight analyte sensing component.

The first hydrophilic copolymer of the first solution includes poly(alkylene oxide) and poly(vinyl pyridine). The copolymer used can contain various combinations and conformations of these polymers to provide the properties desired in the sensing layer, which can include hydrophilicity and the ability to immobilize the analyte sensing component.

In some embodiments, the first hydrophilic copolymer can be a block copolymer. The block copolymer can be various types of block copolymer, such as diblock, triblock, tetrablock, or multiblock copolymer. In some examples the block copolymer has one or more intermediate non-repeating subunits, or junction blocks. In other embodiments, the copolymer can be an alternating, periodic, statistical or graft copolymer. In some instances, the copolymer has two distinct monomer units, such as a diblock copolymer. In other instances, the copolymer has three distinct monomer units, such as a terpolymer.

The poly(alkylene oxide) of the first hydrophilic copolymer can be poly(ethylene glycol), poly(propylene glycol), poly(butylene oxide) or mixture thereof, such as a copolymer that includes a combination of two or three alkylene oxide units. In some embodiments, the poly(alkylene oxide) of the first hydrophilic copolymer can be a block copolymer that includes blocks of two or three poly(alkylene oxide) polymers. In certain embodiments, the poly(alkylene oxide) can be block copolymer of poly(ethylene glycol) and poly(propylene glycol).

In some embodiments, the first hydrophilic copolymer includes a copolymer of poly(ethylene glycol) (PEG) and poly(vinyl pyridine) (PVP). The copolymer of PEG and PVP can be a block copolymer, having one or more blocks each of PEG and PVP. In some embodiments, the first hydrophilic copolymer includes a diblock copolymer of PEG and PVP.

The ratio of PEG to PVP in the first hydrophilic copolymer can be varied depending on the desired properties of the hydrophilic copolymer of the sensing layer. In some instances, the PEG block can have more units on average than the PVP block.

In some embodiments of the method, the first hydrophilic, diblock copolymer has the formula:

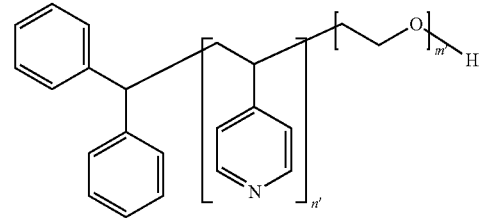

wherein n' and m' are selected to provide the crosslinked, hydrophilic, diblock copolymer of the sensing layer as described herein.

The analyte sensing component of the first solution can be selected based on the analyte desired to be monitored. For example, to monitor physiological cholesterol levels, cholesterol oxidase can be used, and to monitor lactate levels lactate oxidase can be used. To monitor glucose levels, the analyte sensing component used can be glucose oxidase or glucose dehydrogenase (GDH).

In some embodiments of the method, the analyte sensing component includes one or more groups that can chemically react with the first crosslinking agent to form a covalent bond through a linker to the copolymer backbone of the sensing layer. In some instances, the analyte sensing component can be an enzyme having one or more reactive groups, such as an amino, hydroxy or thiol groups, or combination thereof. In some examples, the curing of the first solution provides a crosslinked, hydrophilic copolymer having an immobilized enzyme with one or more oxygen, nitrogen or sulfur atoms covalent bond to the copolymer backbone through a linker. One of skill will recognize that during curing, various linking and crosslinking outcomes are possible. For example, links between two or more analyte sensing components can form, or an analyte sensing component with multiple reactive groups can form multiple links to other analyte sensing components and/or the copolymer backbone.

In other embodiments of the method, the analyte sensing component does not react to form a covalent linkage to the copolymer backbone, but is embedded into the polymer matrix upon curing of the first solution. In certain embodiments, some of the analyte sensing component reacts with the crosslinking agent and some does not react, providing a sensing layer that includes a mixture of immobilized analyte sensing component, where some is embedded in the polymer matrix of the crosslinked, hydrophilic copolymer, and some is covalently bound, optionally through a linker, to the copolymer backbone.

The second solution includes a second hydrophilic copolymer and a second crosslinking agent. The ratio of these components can vary depending on the desired properties of the resulting protective membrane. The second solution can include from about 50% by weight to about 90% by weight second hydrophilic copolymer and from about 10% by weight to about 50% by weight second crosslinking agent.

In some embodiments of the method, the second hydrophilic copolymer includes units of alkylene oxide, vinyl pyridine and one or more other polymerizable moieties, such as styrene, methacrylate and acrylate. In some instances, the copolymer can be a copolymer of alkylene oxide, vinyl pyridine and styrene. The copolymer of alkylene oxide, and styrene can be a block copolymer, having one or more blocks each of poly(alkylene oxide) (PAO), poly(vinyl pyridine) (PVP) and poly(styrene) (PS). In some embodiments, the copolymer includes a triblock copolymer of PAO, PVP and PS. In other embodiments, the copolymer can be a diblock copolymer, where one block includes POA and the other block includes vinyl pyridine and styrene units. In other embodiments, the diblock copolymer can be a PAO capped random copolymer of vinyl pyridine and styrene. In some examples, the PAO caps both ends of the random copolymer, while in other instances one end of the random copolymer is capped with PAO.

The poly(alkylene oxide) of the second hydrophilic copolymer can be poly(ethylene glycol), poly(propylene glycol), poly(butylene oxide) or a mixture thereof, such as a copolymer having a combination of two or three different alkylene oxide units. In some embodiments, the poly(alkylene oxide) of the second hydrophilic copolymer can be a block copolymer including blocks of two or three different poly (alkylene oxide) polymers. In certain embodiments, the poly(alkylene oxide) can be a block copolymer of poly (ethylene glycol) and poly(propylene glycol).

The ratio of alkylene oxide units to vinyl pyridine units to other polymerizable moieties, such as, styrene, methacrylate and acrylate, in the second hydrophilic copolymer can be varied depending on the desired properties of the resulting protective membrane. In some embodiments, the copolymer can have a lesser proportion of alkylene oxide to vinyl pyridine and/or other polymerizable moieties, such as, styrene, methacrylate and acrylates. In some embodiments, the second hydrophilic copolymer can be similar in structure to the hydrophilic copolymer of the first solution.

In some embodiments of the method, the second hydrophilic, diblock copolymer has the formula:

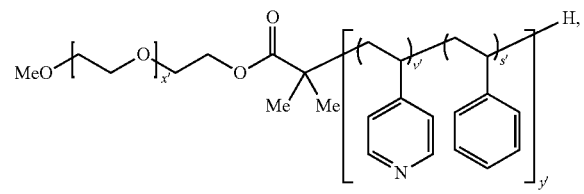

wherein x', y', v' and s' are selected to provide the crosslinked, hydrophilic, diblock copolymer of the sensing layer as described herein.

The first solution or second solution can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis (2-hydroxyethyl)glycine (Bicine), tris(hydroxymethyl) methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis (2-ethanesulfonic acid) (PIPES), dimethylarsinic acid (Cacodylate), saline sodium citrate (SSC), 2-(N-morpholino)ethanesulfonic acid (MES), 2(R)-2-(methylamino) succinic acid, or phosphate buffered saline (PBS). In some embodiments, the first or second solution can be formed in a mixture of a buffered aqueous solution and ethanol.

The first solution or second solution can further include components that aid in the formation of a homogeneous solution or facilitate formation of a sensing layer or protective membrane with specific properties. A component can be added to aid in the dissolution of the other components or to achieve a desired concentration of the other components. A component can also be added to provide a sensing layer or protective layer with desired optical properties. For example, a dye can be added to provide a tinted or colored sensing layer or protective membrane.

The first and second crosslinking agents can be of the same structure, but in some instances, have different structures. Because the first and second crosslinking agents share similar hydrophilic characteristics, they will herein be referred to as "the crosslinking agent".

The crosslinking agent can have two or more reactive groups, such as bi-, tri-, or tetra-functional crosslinking agents that undergo chemical reaction with the crosslinkable functionalities of analyte sensing component of the first solution, and/or the copolymer second solution. In certain embodiments, the crosslinking agent reacts with amine functionalities of the first and/or second copolymer, such as pyridine groups. In other embodiments, the crosslinking agent reacts with amino, hydroxy or thiol functionalities, or a combination thereof, of the analyte sensing component.

The crosslinking agent has a hydrophilic portion that can be water soluble or soluble in a water-miscible solvent, such as an alcohol. The hydrophilic portion of the crosslinking agent can have one or more heteroatoms, for example, nitrogen, oxygen or sulfur atoms.

In some embodiments of the method, the crosslinking agent includes poly(ethylene glycol) (PEG) and two or more reactive groups at the termini of the PEG. For example, the crosslinking agent can be a PEG diglycidyl ether of the formula:

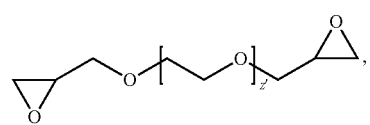

wherein z' is selected to provide the crosslinks of the sensing layer and protective membrane as described herein.

Examples of suitable crosslinking agents include, but are not limited to, diglycidyl ether and N,N-diglycidyl-4-glycidyloxyaniline.

Depositing the first or second solution onto a surface of an electrode or sensing layer, respectively, can be accomplished by a number of methods, and can provide a relatively flat surface of substantially uniform thickness. The depositing can be performed manually with a micro-syringe, or by automated fabrication processes with nano jet dispensing equipment.

In some embodiments of the method, the amount of the first and/or second solution deposited onto a surface of an electrode and/or the sensing layer, respectively, can be selected to provide the desired thickness of the sensing layer and/or the protective membrane. In some embodiments, the amount deposited on the electrode can be about 50 nL/mm$^2$ to about 500 nL/mm$^2$. In other examples, the amount can be about 50 μm to about 150 μm, or about 150 μm to about 300 μm, or about 300 μm to about 500 μm in thickness. In some embodiments, the amount can be about 150 nL/mm$^2$. In some instances, depositing about 150 nL/mm$^2$ of the first solution onto a surface of an electrode provides a sensing layer that is about 2 μm in thickness after curing. In other instances, depositing about 150 nL/mm$^2$ of the second solution onto a surface of the sensing layer provides a protective membrane that is about 2 μm in thickness after curing.

Conditions suitable to promote chemical reaction between the first crosslinking agent and the analyte sensing component and/or first hydrophilic copolymer of the first solution can be selected based on components of the solution being crosslinked and/or linked, but not to degrade the analyte sensing component. In embodiments where the analyte sensing component is an enzyme, the temperature and pH of the method can be selected to preserve the activity of the enzyme.

Conditions used for crosslinking and/or linking in the first solution are selected to promote chemical reaction between the reactive groups of the first crosslinking agent and the reactive groups of the analyte sensing component and/or first hydrophilic copolymer. When the first hydrophilic copolymer and/or analyte sensing component have nitrogen-containing crosslinkable groups (e.g., pyridinyl and amino groups, respectively), conditions can be selected to promote crosslinking and/or linking between the nitrogen and the reactive group of the first crosslinking agent. When the reactive group is an epoxide, the nitrogen of the first hydrophilic copolymer and/or analyte sensing component can undergo nucleophilic attack at one of the electrophilic epoxide carbon atoms, providing a crosslink or linker, respectively, having one or more secondary alcohol moieties. Likewise, conditions can be selected to promote reaction between the second crosslinking agent and the second hydrophilic copolymer in the second solution.

The order of the depositing and the curing can be modified depending on the curing conditions and the characteristics of the first and second solutions. In some embodiments, the curing of the first and/or second solution can be initiated before the solution is deposited. In other instances, the curing of the first and/or second solution can be initiated after the solution is deposited.

In some embodiments, the depositing and curing can be repeated multiple times to obtain a protective membrane of certain thickness and/or composition. In some instances, the first protective layer is about 2 μm in thickness. A third solution including a third hydrophilic copolymer according to the hydrophilic copolymer of the second solution can be formed and deposited, this time on the first cured protective membrane layer, and cured to provide a second layer of protective membrane. In some embodiments, the third solution has the same hydrophilic copolymer and/or crosslinking agent as the second solution. In other instances, the hydrophilic copolymer and/or crosslinking agent of the second and third solutions are different. Depending on the components of the second and third solutions and the curing method, there can be crosslinks between the first and second protective layers. In other instances, the use of different second and third solutions provides different protective membrane layers.

In some embodiments, the protective membrane can be about 1 μm to about 20 μm in thickness. In other embodiments, the protective membrane can be about 1 μm to about 5 μm, or about 10 μm to about 15 μm, or about 15 μm to about 20 μm in thickness. In certain embodiments, repeated depositing and curing of the second and/or third solutions can add about 2 μm of thickness to the previous protective membrane. In some instances, the repeated depositing and curing results in a protective membrane that is 5-10 μm in thickness.

Examples

Example 1

Immobilization of GOx in a Crosslinked Poly(Vinyl Pyridine) (PVP) and Poly(Ethylene Glycol) (PEG) Diblock Copolymer: Formation of the Sensing Layer

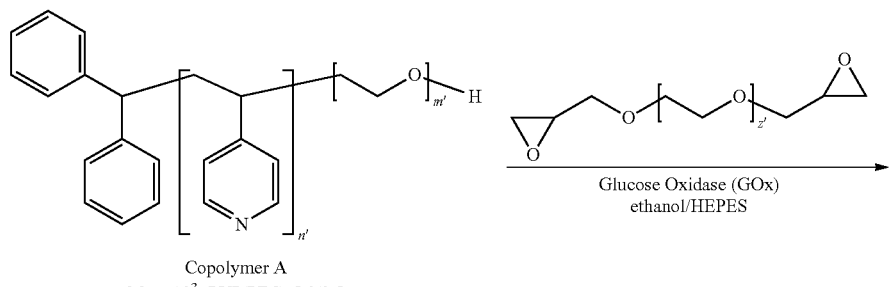

Copolymer A
Mn x 10$^3$: PVP/PEG: 5.0/8.5

Glucose Oxidase (GOx)
ethanol/HEPES

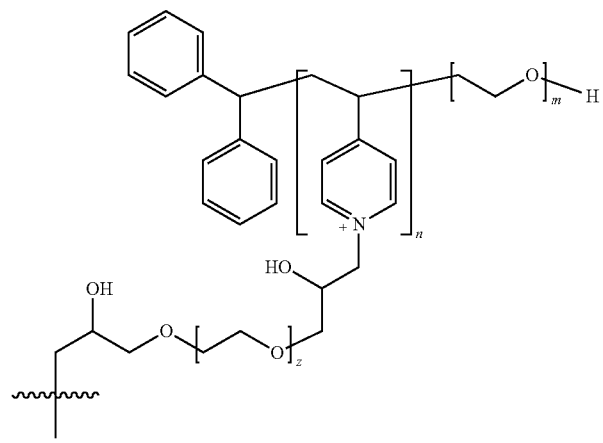

Three solutions were made using a solvent containing 35% (v/v) ethanol and 65% (v/v) 20 mM HEPES buffer (pH=8.0): (A) 20 mg/ml GOx; (B) 20 mg/ml crosslinker (z'=10, PEG (400) diglycidyl ether); (C) 20 mg/ml Diblock Copolymer A (Purchased from Polymer Source, product ID: P8382-4VPEO). The three solutions with the volume ratio: A:B:C=0.3:0.25:0.45 were mixed on a rocker for 2 hours at ambient lab temperature to let the crosslinking reaction to occur. The solution mixture was then deposited on the electrode surface using micro-syringe. The deposited amount was 150 nL per mm². After air-drying, the electrode was further cured for 12 hours at ambient lab temperature. The resulting GOx layer had a thickness of about 2 μm.

Example 2

Formation of a Crosslinked, Poly(Alkylene Oxide) Capped Random Copolymer of Vinyl Pyridine and Styrene Over the Sensing Layer: Formation of the Protective Membrane

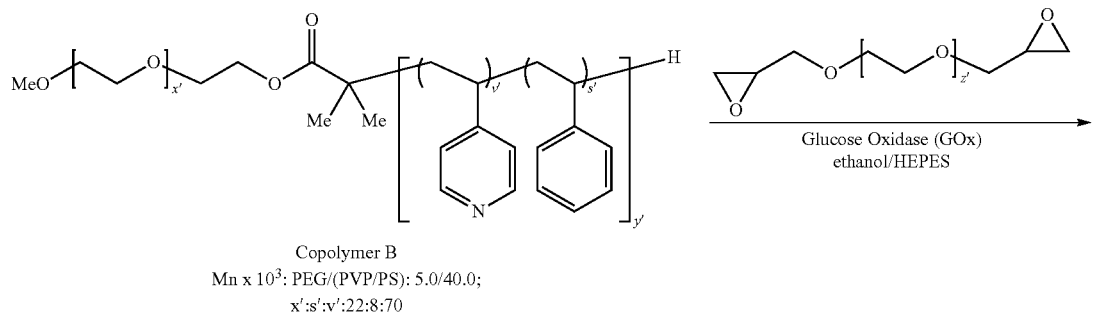

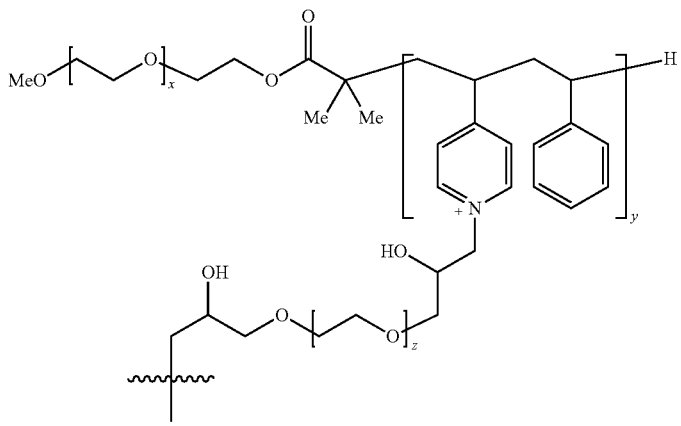

A solution of diblock Copolymer B (20 mg/ml in 85% ethanol-15% HEPES buffer, pH=8) (Purchased from Polymer Source, product ID:P14260-EOS4VPran) was mixed with a solution of crosslinker (20 mg/ml in 85% ethanol-15% HEPES, pH=8) at a copolymer:crosslinker ratio of 0.9:0.1. The mixture was mixed for 2 hours and 150 nL/mm² was deposited onto the layer formed in Example 1, followed by air-drying and further curing for 12 hours at ambient lab temperature. The resulting membrane had a thickness of about 2 μm. The procedure can be repeated to increase the thickness of the membrane.

Example 3

Analyte Sensor Performance in a Glucose Solution

The analyte sensor formed in Example 2 was tested at concentrations of glucose in phosphate buffered saline (PBS) ranging from 20 μm to 1000 μm. The sensor was submerged in PBS and the glucose concentration was increased every 5-10 minutes. The current generated at the electrode was measured using a potentiostat. A linear relationship between current and glucose concentration was observed. See FIG. 1.

Although the crosslinked, hydrophilic copolymers in the above examples include methacrylate groups, there are a number of ethylenically unsaturated groups known in the art to be capable of undergoing polymerization. Ethylenically unsaturated monomers and macromers may be either acrylic- or vinyl-containing Vinyl-containing monomers contain the vinyl grouping ($CH_2$=CH—), and are generally highly reactive. Acrylic-containing monomers are represented by the formula:

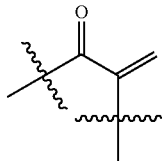 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

The invention claimed is:

1. An analyte sensor comprising:
a sensing layer in contact with a surface of an electrode, wherein the sensing layer comprises a first crosslinked, hydrophilic, diblock copolymer having an immobilized analyte sensing component, wherein the first diblock copolymer comprises a first block of poly(alkylene oxide) and a second block of poly(vinyl pyridine); and
a protective membrane comprising a second crosslinked, hydrophilic, diblock copolymer, wherein the second diblock copolymer comprises a poly(alkylene oxide) capped random copolymer of vinyl pyridine and styrene.

2. The sensor according to claim 1, wherein the first crosslinked, hydrophilic diblock copolymer having the formula:

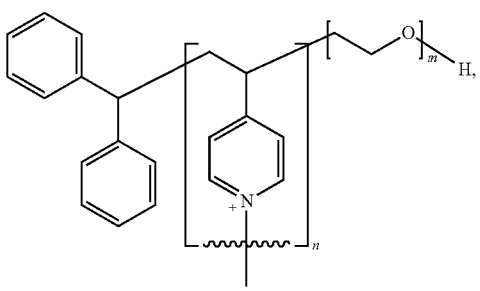

wherein n and m are such that the poly(vinyl pyridine) block and the poly(ethylene glycol) block each have a number average molecular weight ($M_n$) of about 500 to about 10,000.

3. The sensor according to claim 1, wherein the second crosslinked, hydrophilic diblock copolymer has the formula:

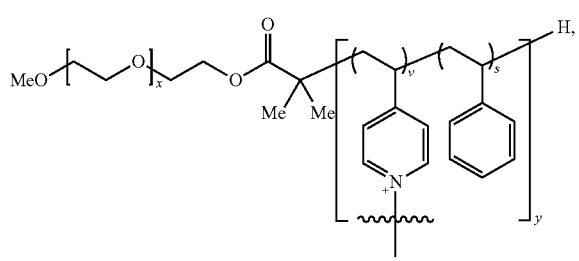

wherein x, y, v and s are such that the poly(ethylene glycol) block and the vinyl pyridine/styrene copolymer block each have a number average molecular weight ($M_n$) of about 1,000 to about 100,000.

4. The sensor according to claim 1, wherein the sensing layer or the protective membrane has crosslinks of the formula:

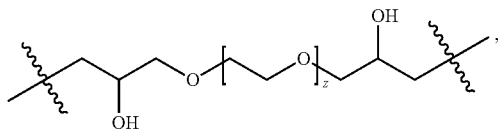

wherein z is 0-10.

5. The sensor according to claim 1, wherein the analyte sensing component is glucose oxidase.

6. The sensor according to claim 1, wherein the sensing layer or protective membrane is about 1 μm to about 5 μm in thickness.

7. The sensor according to claim 1, wherein the immobilized analyte sensing component is covalently bound, optionally through a linker, to the first crosslinked, hydrophilic, diblock copolymer.

8. The sensor according to claim 1, wherein the first crosslinked, hydrophilic diblock copolymer has the formula:

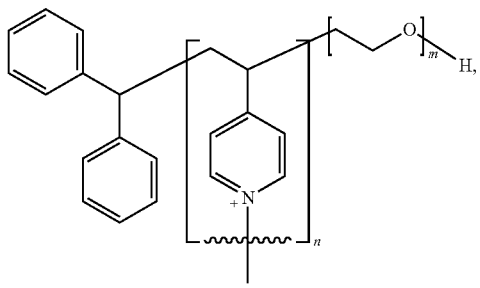

wherein n and m are such that the poly(vinyl pyridine) block has a number average molecular weight ($M_n$) of about 5,000 and the poly(ethylene glycol) block has a number average molecular weight ($M_n$) of about 8,500;
the second crosslinked, hydrophilic diblock copolymer has the formula:

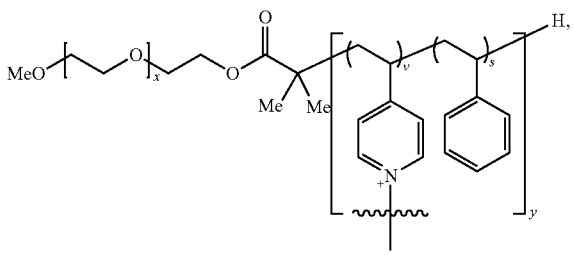

wherein x, y, v and s are such that the poly(ethylene glycol) block has a number average molecular weight ($M_n$) of about 5,000 and the vinyl pyridine/styrene copolymer block has a number average molecular weight ($M_n$) of about 40,000;
the sensing layer and the protective membrane have crosslinks of the formula:

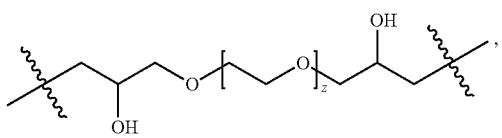

wherein z is 10; and
the analyte sensing component is glucose oxidase.

9. A method for manufacturing an analyte sensor, the method comprising:
forming a first solution of a first hydrophilic, diblock copolymer, a first crosslinking agent and an analyte sensing component, wherein the first hydrophilic, diblock copolymer comprises a first block of poly(alkylene oxide) and second block of poly(vinyl pyridine);
depositing the first solution onto a surface of an electrode;
curing the first solution to provide a sensing layer;
forming a second solution of a second hydrophilic, diblock copolymer and a second crosslinking agent, wherein the second hydrophilic, diblock copolymer comprises a poly(alkylene oxide) capped random copolymer of vinyl pyridine and styrene;
depositing the second solution onto a surface of the sensing layer; and curing the second solution to provide a protective membrane.

10. The method of claim 9, wherein the first hydrophilic, diblock copolymer has the formula:

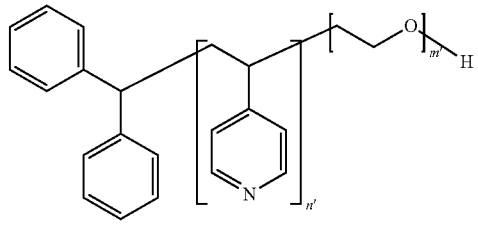

wherein n' and m' are selected such that the poly(vinyl pyridine) block and the poly(ethylene glycol) block each have a number average molecular weight ($M_n$) of about 500 to about 10,000.

11. The method of claim 9, wherein the second hydrophilic, diblock copolymer has the formula:

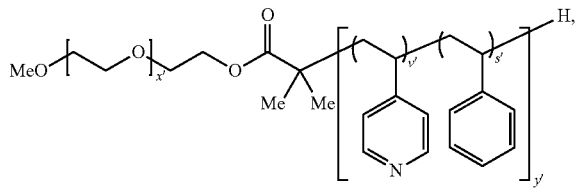

wherein x', y', v' and s' are selected such that the poly(ethylene glycol) block and the vinyl pyridine/styrene copolymer block each have a number average molecular weight ($M_n$) of about 1,000 to about 100,000.

12. The method of claim 9, wherein the first or second crosslinking agent has the formula:

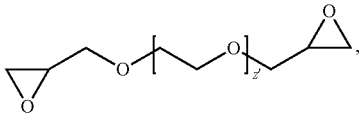

wherein z' is 0-10.

13. The method of claim 9, wherein the sensing layer or the protective membrane is about 1 μm to about 5 μm in thickness.

14. The method of claim 9, wherein the analyte sensing component is glucose oxidase.

15. The method of claim 9, wherein the second solution comprises about 90% by weight second hydrophilic, diblock copolymer and about 10% by weight second crosslinking agent.

16. The method of claim 9, wherein the forming, depositing, and curing of the second solution is repeated to increase the thickness of the protective membrane.

17. The method of claim 9, wherein the amount of analyte sensing component is about 10% by weight to about 40% by weight of the first solution.

18. The method of claim 9, wherein the amount of first crosslinking agent is about 20% by weight to about 30% by weight of the first solution.

19. The method of claim 9, wherein the amount of first hydrophilic, diblock copolymer is about 20% by weight to about 70% by weight of the first solution.

* * * * *